United States Patent
Paliard et al.

(10) Patent No.: US 6,562,346 B1
(45) Date of Patent: May 13, 2003

(54) ACTIVATION OF HCV-SPECIFIC T CELLS

(75) Inventors: Xavier Paliard, San Francisco, CA (US); Michael Houghton, Danville, CA (US); Mark Selby, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/698,874

(22) Filed: Oct. 27, 2000

Related U.S. Application Data

(60) Provisional application No. 60/161,713, filed on Oct. 27, 1999.

(51) Int. Cl.[7] .................. A61K 39/29; A61K 39/12; A61K 38/12; C07K 14/00; C07K 14/08
(52) U.S. Cl. ................. 424/189.1; 424/192.1; 424/194.1; 424/199.1; 424/228.1; 530/300; 530/350; 514/12
(58) Field of Search ............... 424/189.1, 192.1, 424/199.1, 194.1, 228.1; 514/12; 530/300, 350

(56) References Cited

U.S. PATENT DOCUMENTS

| | | |
|---|---|---|
| 5,683,864 A | 11/1997 | Houghton et al. |
| 5,747,239 A * | 5/1998 | Wang et al. .................. 435/5 |
| 5,843,752 A * | 12/1998 | Dasmahapatra et al. .... 435/219 |

FOREIGN PATENT DOCUMENTS

| WO | WO 97/44469 | 11/1997 |
|---|---|---|

OTHER PUBLICATIONS

Nelson et al. J. Immunol. 1997, vol. 97, pp. 1473–1481.*
Koziel et al. J. Clin. Invest. 1995, vol. 96, pp. 2311–2321.*
Diepolder et al. J. Virol. 1997, vol. 71, pp. 6011–6013.*
Erikson et al. J. Immunol. 1993, vol. 151, pp. 4189–4199.*
Chien et al. J. Clinical Microb. 1999, vol. 37, pp. 1393–1397.*
Cerny et al. J. Clin. Invest. 1995, vol. 95, pp. 521–530.*
Bartenschlager et al. Intervirology 1997, vol. 40, pp. 378–393.*
Bartenschlager et al. J. Gene virol. 2000, vol. 81, pp. 1613–1548.*
Shintaro et al. Chem. Pharm. Bull. 1996, vol. 19, pp. 1254–1260.*
Minutelo et al. J. Exp. Med. 1993, vol. 178, pp. 17–25.*
Choe et al., "Enhanced Cellular Immunity to Hepatitis C Virus Nonstructural Proteins by Codelivery of Granulocyte Macrophage–Colony Stimulating Factor Gene in Intramuscular DNA Immunization," *Vaccine* 17:1136–1144 (1999).

* cited by examiner

*Primary Examiner*—James Housel
*Assistant Examiner*—Bao Qun Li
(74) *Attorney, Agent, or Firm*—Alisa A. Harbin; Robert P. Blackburn; Roberta L. Robins

(57) ABSTRACT

The invention provides a method of activating hepatitis C virus (HCV)-specific T cells, including $CD4^+$ and $CD8^+$ T cells. HCV-specific T cells are activated using fusion proteins comprising HCV NS3, NS4, NS5a, and NS5b polypeptides, polynucleotides encoding such fusion proteins, or polypeptide or polynucleotide compositions containing the individual components of these fusions. The method can be used in model systems to develop HCV-specific immunogenic compositions, as well as to immunize a mammal against HCV.

26 Claims, 2 Drawing Sheets

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: CTL
      epitopic peptide from HCV NS5a

<400> SEQUENCE: 1

His Glu Tyr Pro Val Gly Ser Gln Leu
  1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: CD4+
      epitopic peptide from HCV NS5a

<400> SEQUENCE: 2

Ala Glu Leu Ile Glu Ala Asn Leu Leu Trp Arg Gln Glu Met Gly
  1               5                  10                  15
```

ACTIVATION OF HCV-SPECIFIC T CELLS

CROSS-REFERENCE TO RELATED APPLICATION

This application is related to provisional patent application serial No. 60/161,713, filed Oct. 27, 1999, from which priority is claimed under 35 USC §119(e)(1) and which is incorporated herein by reference in its entirety.

TECHNICAL AREA OF THE INVENTION

The invention relates to the activation of hepatitis C virus(HCV)-specific T cells. More particularly, the invention relates to the use of multiple HCV polypeptides, either alone or as fusions, to stimulate cell-mediated immune responses, such as to activate HCV-specific T cells.

BACKGROUND OF THE INVENTION

Hepatitis C virus (HCV) infection is an important health problem with approximately 1% of the world's population infected with the virus. Over 75% of acutely infected individuals eventually progress to a chronic carrier state that can result in cirrhosis, liver failure, and hepatocellular carcinoma. See Alter et al. (1992) N. Engl. J. Med. 327:1899–1905; Resnick and Koff. (1993) Arch. Intem. Med. 153:1672–1677; Seeff (1995) Gastrointest. Dis. 6:20–27; Tong et al. (1995) N. Engl. J. Med. 332:1463–1466.

Despite extensive advances in the development of pharmaceuticals against certain viruses like HIV, control of acute and chronic HCV infection has had limited success (Hooffiagle and di Bisceglie (1997) N. Engl. J. Med. 336:347–356). In particular, generation of a strong cytotoxic T lymphocyte (CTL) response is thought to be important for the control and eradication of HCV infections. Thus, there is a need in the art for effective methods of inducing strong CTL responses against HCV.

SUMMARY OF THE INVENTION

It is an object of the invention to provide reagents and methods for activating T cells which recognize epitopes of HCV polypeptides. This and other objects of the invention are provided by one or more of the embodiments described below.

The invention provides HCV proteins useful for activating HCV-specific T cells. One embodiment provides a fusion protein that consists essentially of an NS3, an NS4, and an NS5a polypeptide.

Another embodiment provides a fusion protein that consists essentially of an NS3, an NS4, an NS5a, and NS5b polypeptide of an HCV.

Still another embodiment of the invention provides a fusion protein comprising an NS3, an NS4, an NS5a and optionally an NS5b polypeptide of an HCV. One of the HCV polypeptides is derived from a different strain of HCV than the other polypeptides.

The invention also provides compositions comprising any of these fusion proteins and a pharmaceutically acceptable carrier.

Another embodiment provides a composition consisting essentially of an NS3, an NS4, and an NS5a polypeptide, or a composition consisting essentially of polynucleotides encoding the individual proteins.

Another embodiment provides a composition that consists essentially of an NS3, an NS4, an NS5a, and NS5b polypeptide of an HCV, or a composition consisting essentially of polynucleotides encoding the individual proteins.

Still another embodiment of the invention provides a composition consisting essentially of an NS3, an NS4, an NS5a and optionally an NS5b polypeptide of an HCV, or a composition consisting essentially of polynucleotides encoding the individual proteins. One of the HCV polypeptides or polynucleotides is derived from a different strain of HCV than the others.

Even another embodiment of the invention provides an isolated and purified polynucleotide which encodes a fusion protein consisting essentially of an NS3, an NS4, and an NS5a polypeptide of an HCV or a fusion protein consisting essentially of an NS3, an NS4, an NS5a, and an NS5b polypeptide of an HCV.

Yet another embodiment of the invention provides a composition comprising an isolated and purified polynucleotide which encodes a fusion protein consisting essentially of either an NS3, an NS4, and an NS5a polypeptide of an HCV or consisting essentially of an NS3, an NS4, an NS5a, and an NS5b polypeptide of an HCV. The composition also comprises a pharmaceutically acceptable carrier.

Another embodiment of the invention provides isolated and purified polynucleotide which encodes a fusion protein comprising an NS3, an NS4, and an NS5a polypeptide of an HCV in which one of the NS3, NS4, and NS5a polypeptides is derived from a different strain of HCV than the other two polypeptides. The invention also provides a composition comprising this polynucleotide and a pharmaceutically acceptable carrier.

Yet another embodiment of the invention provides an isolated and purified polynucleotide which encodes a fusion protein comprising an NS3, an NS4, an NS5a, and an NS5b polypeptide of an HCV. One of the polypeptides is derived from a different strain of HCV than the other polypeptides. The invention also provides a composition comprising this polynucleotide and a pharmaceutically acceptable carrier.

Even another embodiment of the invention provides a method of activating T cells which recognize an epitope of an HCV polypeptide. T cells are contacted with a fusion protein comprising an NS3, an NS4, and an NS5a polypeptide of an HCV. A population of activated T cells recognizes an epitope of the NS3, NS4, or NS5a polypeptide. Alternatively, T cells are contacted with a fusion protein comprising an HCV NS3, NS4, NS5a, NS5b polypeptide of an HCV. A population of activated T cells recognizes an epitope of the NS3, NS4, NS5a, or NS5b polypeptide.

The invention thus provides methods and reagents for activating T cells which recognize epitopes of HCV polypeptides. These methods and reagents are particularly advantageous for identifying epitopes of HCV polypeptides associated with a strong CTL response and for immunizing mammals, including humans, against HCV.

BRIEF DESCRIPTION OF THE FIGURES

FIG. 1 shows a side-by-side comparison of IFN-γ expression generated in animals in response to delivery of alphavirus constructs encoding NS3NS4NS5a.

DETAILED DESCRIPTION OF THE INVENTION

Figure 1:
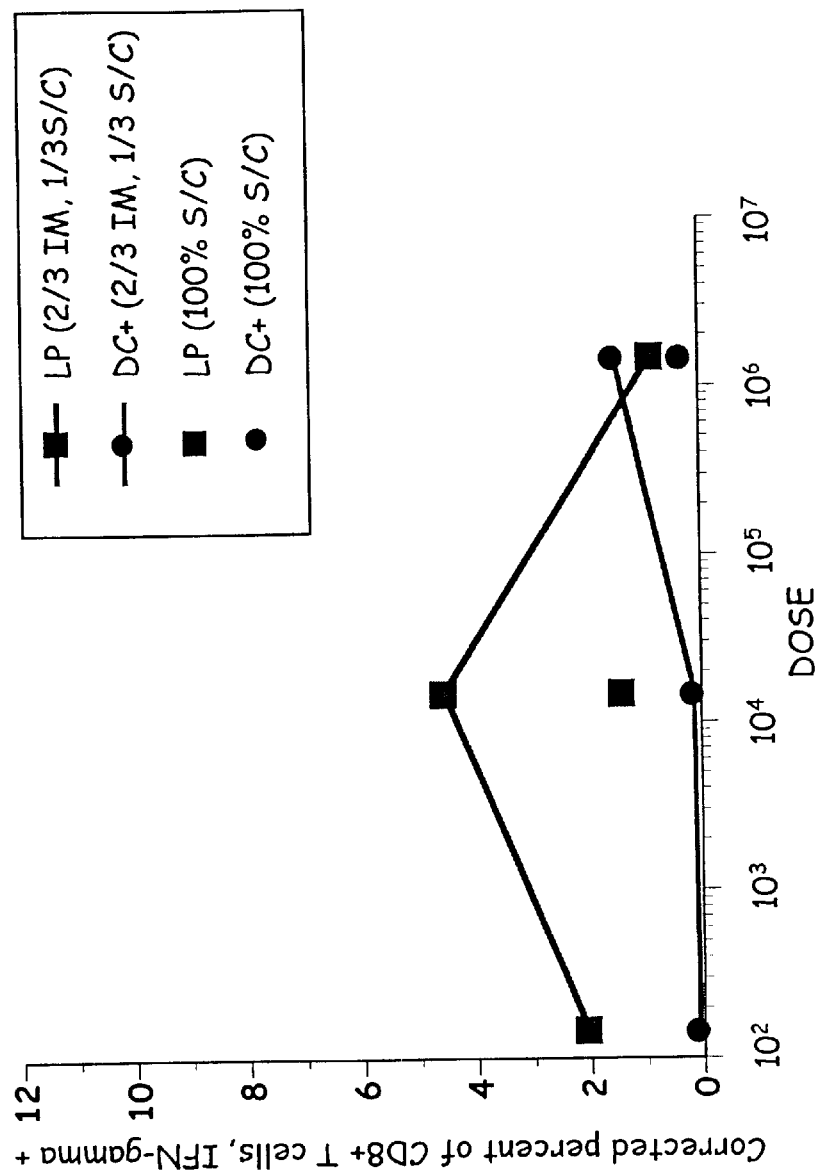

The practice of the present invention will employ, unless otherwise indicated, conventional methods of chemistry, biochemistry, recombinant DNA techniques and immunology, within the skill of the art. Such techniques are explained fully in the literature. See, e.g., Sambrook, et al., *Molecular Cloning: A Laboratory Manual* (2nd Edition); *Methods In Enzymology* (S. Colowick and N. Kaplan eds., Academic Press, Inc.); *DNA Cloning,* Vols. I and II (D. N. Glover ed.); *Oligonucleotide Synthesis* (M. J. Gait ed.); *Nucleic Acid Hybridization* (B. D. Hames & S. J. Higgins eds.); *Animal Cell Culture* (R. K. Freshney ed.); Perbal, B., *A Practical Guide to Molecular Cloning.*

All publications, patents and patent applications cited herein, whether supra or infra, are hereby incorporated by reference in their entirety. It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains, such as from strains 1, 2, 3 or 4 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS4" polypeptide refers to native NS4 from any of the various HCV strains, as well as NS4 analogs, muteins and immunogenic fragments, as defined further below.

The terms "analog" and "mutein" refer to biologically active derivatives of the reference molecule, or fragments of such derivatives, that retain desired activity, such as the ability to stimulate a cell-mediated immune response, as defined below. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the full-length sequence, provided that the fragment in question retains immunogenic activity, as measured by the assays described herein. For a description of various HCV epitopes, see, e.g., Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; commonly owned, allowed U.S. patent application Ser. Nos. 08/403,590 and 08/444,818.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety.

An "immunological response" to an HCV antigen (including both polypeptide and polynucleotides encoding polypeptides that are expressed in vivo) or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J. Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

A "nucleic acid" molecule or "polynucleotide" can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature.

The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means at least 75% by weight, more preferably at least 85% by weight, more preferably still at least 95% by weight, and most preferably at least 98% by weight, of biological macromolecules of the same type are present.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98%, or more, sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

It is a discovery of the present invention that fusion proteins, combinations of the individual components of these fusions, and polynucleotides encoding the same, comprising an NS3, an NS4, and an NS5a polypeptide or an NS3, an NS4, an NS5a, and an NS5b polypeptide of an HCV virus can be used to activate HCV-specific T cells, i.e., T cells which recognize epitopes of these polypeptides. Activation of HCV-specific T cells by such fusion polypeptides and proteins, or combinations of the individual polypeptides that make up the fusions, provide both in vitro and in vivo model systems for the development of HCV vaccines, particularly for identifying HCV polypeptide epitopes associated with a response. The fusion proteins, or combinations of the individual proteins, can also be used to generate an immune response against HCV in a mammal, particularly a CTL response for either therapeutic or prophylactic purposes.

NS3NS4NS5a and NS3NS4NS5aNS5b Fusion Proteins

The genomes of HCV strains contain a single open reading frame of approximately 9,000 to 12,000 nucleotides, which is transcribed into a polyprotein. An HCV polyprotein is cleaved to produce at least ten distinct products, in the order of $NH_2$-Core-E1-E2-p7-NS2-NS3-NS4a-NS4b-NS5a-NS5b-COOH. Fusion proteins of the invention (NS3NS4NS5a fusion proteins, also termed "NS345a" herein) comprise HCV NS3, NS4 (NS4a and NS4b), and NS5a polypeptides or comprise HCV NS3, NS4 (NS4a and NS4b), NS5a, and NS5b polypeptides (NS3NS4NS5aNS5b fusion proteins, also termed "NS345ab" herein). Other fusions described in the examples include fusions of HCV NS3 and NS4 (NS4a and NS4b, also termed "NS34" and "NS34ab"); as well as fusions of HCV NS3 and NS4a (also termed "NS34a").

The HCV NS3 protein functions as a protease and a helicase and occurs at approximately amino acid 1027 to amino acid 1657 of the polyprotein (numbered relative to HCV-1). See Choo et al. (1991) Proc. Natl. Acad. Sci. USA 88:2451–2455. HCV NS4 occurs at approximately amino acid 1658 to amino acid 1972, NS5a occurs at approximately amino acid 1973 to amino acid 2420, and HCV NS5b occurs at approximately amino acid 2421 to amino acid 3011 of the polyprotein (numbered relative to HCV-1) (Choo et al., 1991).

The NS3, NS4, NS5a, and NS5b polypeptides present in the various fusions described above can either be full-length polypeptides or portions of NS3, NS4 (NS4a and NS4b), NS5a, and NS5b polypeptides. The portions of NS3, NS4, NS5a, and NS5b polypeptides making up the fusion protein comprise at least one epitope, which is recognized by a T cell receptor on an activated T cell, such as 2152-HEYPVGSQL-2160 (SEQ ID NO:1) and 2224-AELIEANLLWRQEMG-2238 (SEQ ID NO:2). Epitopes of NS3, NS4 (NS4a and NS4b), NS5a, NS5b, NS3NS4NS5a, and NS3NS4NS5aNS5b can be identified by several methods. For example, NS3, NS4, NS5a, NS5b polypeptides or fusion proteins comprising any combination of the above, can be isolated, for example, by immunoaffinity purification using a monoclonal antibody for the polypeptide or protein. The isolated protein sequence can then be screened by preparing a series of short peptides by proteolytic cleavage of the purified protein, which together span the entire protein sequence. By starting with, for example, 100-mer polypeptides, each polypeptide can be tested for the presence of epitopes recognized by a T cell receptor on an HCV-activated T cell, progressively smaller and overlapping fragments can then be tested from an identified 100-mer to map the epitope of interest.

Epitopes recognized by a T cell receptor on an HCV-activated T cell can be identified by, for example, $^{51}Cr$ release assay (see Example 2) or by lymphoproliferation assay (see Example 4). In a $^{51}Cr$ release assay, target cells can be constructed that display the epitope of interest by cloning a polynucleotide encoding the epitope into an expression vector and transforming the expression vector into the target cells. HCV-specific $CD8^+$ T cells will lyse target cells displaying an NS3, NS4, NS5a, NS5b, NS3NS4NS5a, or NS3NS4NS5aNS5b epitope and will not lyse cells that do not display such an epitope. In an lymphoproliferation assay, HCV-activated $CD4^+$ T cells will proliferate when cultured with an NS3, NS4, NS5a, NS5b, NS3NS4NS5a, or NS3NS4NS5aNS5b epitopic peptide, but not in the absence of an HCV epitopic peptide.

NS3, NS4, NS5a, and NS5b polypeptides can occur in any order in the fusion protein. If desired, at least 2, 3, 4, 5, 6, 7, 8, 9, or 10 or more of one or more of the polypeptides may occur in the fusion protein. Multiple viral strains of HCV occur, and NS3, NS4, NS5a, and NS5b polypeptides of any of these strains can be used in a fusion protein.

Nucleic acid and amino acid sequences of a number of HCV strains and isolates, including nucleic acid and amino acid sequences of NS3, NS4, NS5a, NS5b genes and polypeptides have been determined. For example, isolate HCV J1.1 is described in Kubo et al. (1989) Japan. Nucl. Acids Res. 17:10367–10372; Takeuchi et al. (1990) Gene 91:287–291; Takeuchi et al. (1990) J. Gen. Virol. 71:3027–3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524–9528 and Takamizawa et al., (1991) J. Virol. 65:1105–1113 respectively.

Publications that describe HCV-1 isolates include Choo et al. (1990) Brit. Med. Bull. 46:423–441; Choo et al. (1991) Proc. Natl. Acad. Sci. USA 88:2451–2455 and Han et al. (1991) Proc. Natl. Acad. Sci. USA 88:1711–1715. HCV isolates HC-J1 and HC-J4 are described in Okamoto et al. (1991) Japan J. Exp. Med. 60:167–177. HCV isolates HCT 18~, HCT 23, Th, HCT 27, EC1 and EC10 are described in Weiner et al. (1991) Virol. 180:842–848. HCV isolates Pt-1, HCV-K1 and HCV-K2 are described in Enomoto et al. (1990) Biochem. Biophys. Res. Commun. 170:1021–1025. HCV isolates A, C, D & E are described in Tsukiyama-Kohara et al. (1991) Virus Genes 5:243–254.

Each of the NS3, NS4, NS5a, and NS5b components of a fusion protein can be obtained from the same HCV strain or isolate or from different HCV strains or isolates. Fusion proteins comprising HCV polypeptides from, for example, the NS3 polypeptide can be derived from a first strain of HCV, and the NS4, and NS5a polypeptides can be derived from a second strain of HCV. Alternatively, the NS4 polypeptide can be derived from a first strain of HCV, and the NS3 and NS5a polypeptides can be derived from a second strain of HCV. Optionally, the NS5a polypeptide can be derived from a first strain of HCV, and the NS3 and NS4 polypeptides can be derived from a second strain of HCV, NS3, NS4 and NS5a polypeptides that are each be derived from different HCV strains can also be used in an NS3NS4NS5a fusion protein. Similarly, in a fusion protein comprising NS5b, at least one of the NS3, NS4, NS5a, and NS5b polypeptides can be derived from a different HCV strain than the other polypeptides. Optionally, NS3, NS4, NS5a, and NS5b polypeptides that are each derived from different HCV strains can also be used in an NS3NS4NS5aNS5b fusion protein.

In addition to NS3, NS4a, NS4b, NS5a and NS5b, the fusion proteins can contain other polypeptides derived from the HCV polyprotein. For example, it may be desirable to include polypeptides derived from the core region of the HCV polyprotein. This region occurs at amino acid positions 1–191 of the HCV polyprotein, numbered relative to HCV-1. Either the full-length protein or epitopes of the full-length protein may be used in the subject fusions, such as those epitopes found between amino acids 10–53, amino acids 10–45, amino acids 67–88, amino acids 120–130, or any of the core epitopes identified in, e.g., Houghton et al., U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and commonly owned, allowed U.S. patent application Ser. Nos. 08/403,590 and 08/444,818, the disclosures of which are incorporated herein by reference in their entireties.

Preferably, the above-described fusion proteins, as well as the individual components of these proteins, are produced recombinantly. A polynucleotide encoding these proteins can be introduced into an expression vector which can be expressed in a suitable expression system. A variety of bacterial, yeast, mammalian and insect expression systems are available in the art and any such expression system can be used. Optionally, a polynucleotide encoding these proteins can be translated in a cell-free translation system. Such methods are well known in the art. The proteins also can be constructed by solid phase protein synthesis.

If desired, the fusion proteins, or the individual components of these proteins, also can contain other amino acid sequences, such as amino acid linkers or signal sequences, as well as ligands useful in protein purification, such as glutathione-S-transferase and staphylococcal protein A.

NS3NS4NS5a and NS3NS4NS5aNS5b Polynucleotides

Polynucleotides contain less than an entire HCV genome and can be RNA or single- or double-stranded DNA. Preferably, the polynucleotides are isolated free of other components, such as proteins and lipids. NS3NS4NS5a polynucleotides encode the NS3NS4NS5a fusion proteins described above, and thus comprise coding sequences for NS3, NS4, and NS5a polypeptides. NS3NS4NS5aNS5b polynucleotides encode the NS3NS4NS5aNS5b fusion proteins described above, and thus comprise coding sequences for NS3, NS4, NS5a, and NS5b polypeptides. Similarly, polynucleotides encoding other fusions, such as NS3NS4 and NS3NS4a will comprise sequences for the individual HCV polypeptides. Polynucleotides of the invention can also comprise other nucleotide sequences, such as sequences coding for linkers, signal sequences, or ligands useful in protein purification such as glutathione-S-transferase and staphylococcal protein A.

Polynucleotides encoding NS3, NS4, NS5a and/or NS5b can be isolated from a genomic library derived from nucleic acid sequences present in, for example, the plasma, serum, or liver homogenate of an HCV infected individual or can be synthesized in the laboratory, for example, using an automatic synthesizer. An amplification method such as PCR can be used to amplify polynucleotides from either HCV genomic DNA or cDNA encoding NS3, NS4, NS5a, or NS5b.

Polynucleotides encoding NS3, NS4, NS5a, or NS5b polypeptides can comprise coding sequences for these polypeptides which occur naturally or can be artificial sequences which do not occur in nature. These polynucleotides can be ligated to form a coding sequence for the fusion proteins using standard molecular biology techniques. If desired, polynucleotides can be cloned into an expression vector and transformed into, for example, bacterial, yeast, insect, or mammalian cells so that the fusion proteins of the invention can be expressed in and isolated from a cell culture.

The expression constructs of the present invention, including the desired fusion, or individual expression constructs comprising the individual components of these fusions, may be used for nucleic acid immunization, to activate HCV-specific T cells, using standard gene delivery protocols. Methods for gene delivery are known in the art. See, e.g., U.S. Pat. Nos. 5,399,346, 5,580,859, 5,589,466, incorporated by reference herein in their entireties. Genes can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1 Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413–7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76: 145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta.* (1975) 394:483–491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110–2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476).

Molecular conjugate vectors, such as the adenovirus chimeric vectors described in Michael et al., *J. Biol. Chem.* (1993) 268:6866–6869 and Wagner et al., *Proc. Natl. Acad. Sci. USA* (1992) 89:6099–6103, can also be used for gene delivery.

Members of the Alphavirus genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508–519; and International Publication Nos. WO 95/07995 and WO 96/17072.

Other vectors can be used, including but not limited to simian virus 40, cytomegalovirus. Bacterial vectors, such as Salmonella ssp. *Yersinia enterocolitica*, Shigella spp., *Vibrio cholerae*, Mycobacterium strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The expression constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly (lactides) and poly(lactide-co-glycolides), known as PLG. See, e.g., Jeffery et al., *Pharm. Res.* (1993) 10:362–368; and McGee et al., *J. Microencap.* (1996).

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L.,

*Advanced Drug Delivery Reviews* (1990) 5:163–187, for a review of delivery systems useful for gene transfer. One particularly effective method of delivering DNA using electroporation is described in International Publication No. WO/0045823.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Compositions Comprising Fusion Proteins or Polynucleotides

The invention also provides compositions comprising the fusion proteins or polynucleotides, as well as compositions including the individual components of these fusion proteins or polynucleotides. Compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition of the invention, such liposomes are described above.

If desired, co-stimulatory molecules which improve immunogen presentation to lymphocytes, such as B7-1 or B7-2, or cytokines such as GM-CSF, IL-2, and IL-12, can be included in a composition of the invention. Optionally, adjuvants can also be included in a composition. Adjuvants which can be used include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE ), formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribim adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an *E. coli* heat-labile toxin (LT), particularly LT-K63, LT-R72, CT-S109, PT-K9/G129; see, e.g., WO 93/13302 and WO 92/19265; (7) other substances that act as immunostimulating agents to enhance the effectiveness of the composition; and (8) microparticles with adsorbed macromolecules, as described in copending U.S. patent application Ser. No. 09/285,855 (filed Apr. 2, 1999) and international Patent Application Ser. No. PCT/US99/17308 (filed Jul. 29, 1999). Alum and MF59 are preferred.

As mentioned above, muramyl peptides include, but are not limited to, N-acetyl-muramyl-L-threonyl-D-isoglutamine (thr-MDP), -acetyl-normuramyl-L-alanyl-D-isoglutamine (CGP 11637, referred to nor-MDP), N-acetylmuramyl-L-alanyl-D-isoglutaminyl-L-alanine-2-(1 '-2'-dipalmitoyl-sn-glycero-3-hydroxyphosphoryloxy)-ethylamine (CGP 19835A, referred to as MTP-PE), etc.

Methods of Producing HCV-Specific Antibodies

The HCV fusion proteins, such as NS3NS4SN5a and NS3NS4NS5aNS5b fusion proteins, can be used to produce HCV-specific polyclonal and monoclonal antibodies. HCV-specific polyclonal and monoclonal antibodies specifically bind to HCV antigens.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against HCV-specific epitopes present in the fusion proteins can also be readily produced. Normal B cells from a mammal, such as a mouse, immunized with, e.g., an NS3NS4SN5a or an NS3NS4NS5aNS5b fusion protein can be fused with, for example, HAT-sensitive mouse myeloma cells to produce hybridomas. Hybridomas producing HCV-specific antibodies can be identified using RIA or ELISA and isolated by cloning in semi-solid agar or by limiting dilution. Clones producing HCV-specific antibodies are isolated by another round of screening.

Antibodies, either monoclonal and polyclonal, which are directed against HCV epitopes, are particularly useful for detecting the presence of HCV or HCV antigens in a sample, such as a serum sample from an HCV-infected human. An immunoassay for an HCV antigen may utilize one antibody or several antibodies. An immunoassay for an HCV antigen may use, for example, a monoclonal antibody directed towards an HCV epitope, a combination of monoclonal antibodies directed towards epitopes of one HCV polypeptide, monoclonal antibodies directed towards epitopes of different HCV polypeptides, polyclonal antibodies directed towards the same HCV antigen, polyclonal antibodies directed towards different HCV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate HCV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind HCV particles or antigens from a biological sample, such as blood or plasma. The bound HCV particles or antigens are recovered from the column matrix by, for example, a change in pH.

HCV-Specific T cells

HCV-specific T cells that are activated by the above-described fusions, including the NS3NS4NS5a fusion protein or NS3NS4NS5aNS5b fusion protein, expressed in vivo or in vitro, or combinations of the individual components of the fusions, preferably recognize an epitope of an HCV polypeptide such as an NS3, NS4, NS5a, NS5b polypeptide, including an epitope of an NS3NS4NS5a fusion protein or an NS3NS4NS5aNS5b fusion protein. HCV-specific T cells can be $CD8^+$ or $CD4^+$.

HCV-specific $CD8^+$ T cells preferably are cytotoxic T lymphocytes (CTL) which can kill HCV-infected cells that display NS3, NS4, NS5a, NS5b epitopes complexed with an MHC class I molecule. HCV-specific $CD8^+$ T cells may also express interferon-$\gamma$ (IFN-$\gamma$). HCV-specific $CD8^+$ T cells can be detected by, for example, $^{51}$Cr release assays (see Example 2). $^{51}$Cr release assays measure the ability of HCV-specific $CD8^+$ T cells to lyse target cells displaying an NS3, NS4, NS5a, NS5b, NS3NS4NS5a, or NS3NS4NS5aNS5b epitope. HCV-specific $CD8^+$ T cells which express IFN-$\gamma$ can also be detected by immunological methods, preferably by intracellular staining for IFN-$\gamma$ after in vitro stimulation with an NS3, an NS4, an NS5a, or an NS5b polypeptide (see Example 3).

HCV-specific $CD4^+$ cells activated by the above-described fusions, such as an NS3NS4NS5a or NS3NS4NS5aNS5b fusion protein, expressed in vivo or in vitro, and combinations of the individual components of these proteins, preferably recognize an epitope of an NS3, NS4, NS5a, or NS5b polypeptide, including an epitope of an NS3NS4NS5a or NS3NS4NS5aNS5b fusion protein, that is bound to an MHC class II molecule on an HCV-infected cell and proliferate in response to stimulating NS3NS4NS5a or NS3NS4NS5aNS5b peptides.

HCV-specific $CD4^+$ T cells can be detected by a lymphoproliferation assay (see Example 4). Lymphoproliferation assays measure the ability of HCV-specific $CD4^+$ T cells to proliferate in response to an NS3, an NS4, an NS5a, or an NS5b epitope.

Methods of Activating HCV-Specific T Cells

NS3NS4NS5a fusion proteins or polynucleotides and NS3NS4NS5aNS5b fusion proteins or polynucleotides, or combinations of the individual components of these proteins and polynucleotides, can be used to activate HCV-specific T cells either in vitro or in vivo. Activation of HCV-specific T cells can be used, inter alia, to provide model systems to optimize CTL responses to HCV and to provide prophylactic or therapeutic treatment against HCV infection. For in vitro activation, proteins are preferably supplied to T cells via a plasmid or a viral vector, such as an adenovirus vector, as described above.

Polyclonal populations of T cells can be derived from the blood, and preferably from peripheral lymphoid organs, such as lymph nodes, spleen, or thymus, of mammals that have been infected with an HCV. Preferred mammals include mice, chimpanzees, baboons, and humans. The HCV serves to expand the number of activated HCV-specific T cells in the mammal. The HCV-specific T cells derived from the mammal can then be restimulated in vitro by adding HCV NS3NS4NS5a or NS3NS4NS5aNS5b epitopic peptides to the T cells. The HCV-specific T cells can then be tested for, inter alia, proliferation, the production of IFN-$\gamma$, and the ability to lyse target cells displaying NS3NS4NS5a or NS3NS4NS5aNS5b epitopes in vitro.

In a lymphoproliferation assay (see Example 4), HCV-activated $CD4^+$ T cells proliferate when cultured with an NS3, NS4, NS5a, NS5b, NS3NS4NS5a, or NS3NS4NS5aNS5b epitopic peptide, but not in the absence of an epitopic peptide. Thus, particular NS3, NS4, NS5a, NS5b, NS3NS4NS5a and NS3NS4NS5aNS5b epitopes that are recognized by HCV-specific $CD4^+$ T cells can be identified using a lymphoproliferation assay.

Similarly, detection of IFN-$\gamma$ in HCV-specific $CD8^+$ T cells after in vitro stimulation with the above-described fusion proteins, or individual components of these proteins, can be used to identify NS3, NS4, NS5a, NS5b, NS3NS4NS5a, and NS3NS4NS5aNS5b epitopes that particularly effective at stimulating $CD8^+$ T cells to produce IFN-$\gamma$ (see Example 3).

Further, $^{51}$Cr release assays are useful for determining the level of CTL response to HCV. See Cooper et al. Immunity 10:439–449. For example, HCV-specific $CD8^+$ T cells can be derived from the liver of an HCV infected mammal. These T cells can be tested in $^{51}$Cr release assays against target cells displaying, e.g., NS3NS4NS5a NS3NS4NS5aNS5b epitopes. Several target cell populations expressing different NS3NS4NS5a or NS3NS4NS5aNS5b epitopes can be constructed so that each target cell population displays different epitopes of NS3NS4NS5a or NS3NS4NS5aNS5b. The HCV-specific $CD8^+$ cells can be assayed against each of these target cell populations. The results of the $^{51}$Cr release assays can be used to determine which epitopes of NS3NS4NS5a or NS3NS4NS5aNS5b are responsible for the strongest CTL response to HCV. NS3NS4NS5a fusion proteins or NS3NS4NS5aNS5b fusion proteins which contain the epitopes responsible for the strongest CTL response can then be constructed using the information derived from the $^{51}$Cr release assays.

An NS3NS4NS5a or NS3NS4NS5aNS5b fusion protein or polynucleotide encoding such a fusion protein, as well as the individual components of these fusion proteins or polynucleotides, can be administered to a mammal, such as a mouse, baboon, chimpanzee, or human, to activate HCV-specific T cells in vivo. Administration can be by any means known in the art, including parenteral, intranasal, intramuscular or subcutaneous injection, including injection using a biological ballistic gun ("gene gun"), as discussed above.

Preferably, injection of an NS3NS4NS5a or NS3NS4NS5aNS5b polynucleotide, or a compositions containing a combination of the individual components of the fusion polynucleotides, is used to activate T cells. In addition to the practical advantages of simplicity of construction and modification, injection of NS3NS4NS5a or NS3NS4NS5aNS5b polynucleotides results in the synthesis of an NS3NS4NS5a fusion protein or NS3NS4NS5aNS5b, respectively, in the host. Similarly, administration of the individual components of these polynucleotides, such as in a composition consisting essentially of individual polynucleotides encoding NS3, NS4, NS5a or a composition consisting essentially of individual polynucleotides encoding NS3, NS4, NS5a and NS5b, results in the expression of the individual proteins in the host. Thus, these immunogens are presented to the host immune system with native post-translational modifications, structure, and conformation. The polynucleotides are preferably injected intramuscularly to a large mammal, such as a human, at a dose of 0.5, 0.75, 1.0, 1.5, 2.0, 2.5, 5 or 10 mg/kg.

A composition of the invention comprising an NS3NS4NS5a fusion protein or polynucleotide, an NS3NS4NS5aNS5b fusion protein or polynucleotide, combinations of these fusions, or a combination of the individual components thereof, is administered in a manner compatible with the particular composition used and in an amount which is effective to activate HCV-specific T cells as measured by, inter alia, a $^{51}$Cr release assay, a lymphoproliferation assay, or by intracellular staining for IFN-γ. The proteins and/or polynucleotides can be administered either to a mammal which is not infected with an HCV or can be administered to an HCV-infected mammal. The particular dosages of the polynucleotides or fusion proteins in a composition or will depend on many factors including, but not limited to the species, age, and general condition of the mammal to which the composition is administered, and the mode of administration of the composition. An effective amount of the composition of the invention can be readily determined using only routine experimentation. In vitro and in vivo models described above can be employed to identify appropriate doses. The amount of NS3NS4NS5a polynucleotide used in the example described below provides general guidance which can be used to optimize the activation of HCV-specific T cells either in vivo or in vitro. Generally, 0.5, 0.75, 1.0, 1.5, 2.0, 2.5, 5 or 10 mg of an NS3NS4NS5a or NS3NS4NS5aNS5b fusion protein or polynucleotide, or of each of the individual components, will be administered to a large mammal, such as a baboon, chimpanzee, or human. If desired, co-stimulatory molecules or adjuvants can also be provided before, after, or together with the compositions.

Immune responses of the mammal generated by the delivery of a composition of the invention, including activation of HCV-specific T cells, can be enhanced by varying the dosage, route of administration, or boosting regimens. Compositions of the invention may be given in a single dose schedule, or preferably in a multiple dose schedule in which a primary course of vaccination includes 1–10 separate doses, followed by other doses given at subsequent time intervals required to maintain and/or reenforce an immune response, for example, at 1–4 months for a second dose, and if needed, a subsequent dose or doses after several months.

III. Experimental

Below are examples of specific embodiments for carrying out the present invention. The examples are offered for illustrative purposes only, and are not intended to limit the scope of the present invention in any way. Those of skill in the art will readily appreciate that the invention may be practiced in a variety of ways given the teaching of this disclosure.

Efforts have been made to ensure accuracy with respect to numbers used (e.g., amounts, temperatures, etc.), but some experimental error and deviation should, of course, be allowed for.

EXAMPLE 1

Production of NS3NS4NS5a Polynucleotides

A polynucleotide encoding NS3NS4NS5a (approximately amino acids 1027 to 2399, numbered relative to HCV-1) (also termed "NS345a" herein) or NS5a (approximately amino acids 1973 to 2399, numbered relative to HCV-1) was isolated from an HCV. Polynucleotides encoding a methionine residue were ligated to the 5' end of these polynucleotides and the polynucleotides were cloned into plasmid, vaccinia virus, and adenovirus vectors.

Immunization Protocols. In one immunization protocol, mice were immunized with 50 μg of plasmid DNA encoding either NS5a or encoding an NS3NS4NS5a fusion protein by intramuscular injection into the tibialis anterior. A booster injection of $10^7$ pfu of vaccinia virus (VV)-NS5a (intraperitoneal) or 50 μg of plasmid control (intramuscular) was provided 6 weeks later.

In another immunization protocol, mice were injected intramuscularly in the tibialis anterior with $10^{10}$ adenovirus particles encoding an NS3NS4NS5a fusion protein. An intraperitoneal booster injection of $10^7$ pfu of VV-NS5a or an intramuscular booster injection of $10^{10}$ adenovirus particles encoding NS3NS4NS5a was provided 6 weeks later.

EXAMPLE 2

Immunization with DNA encoding an NS3NS4NS5a fusion protein activates HCV-specific CD8$^+$ T cells.

$^{51}$Cr Release Assay. A $^{51}$Cr release assay was used to measure the ability of HCV-specific T cells to lyse target cells displaying an NS5a epitope. Spleen cells were pooled from the immunized animals. These cells were restimulated in vitro for 6 days with the CTL epitopic peptide p214K9 (2152-HEYPVGSQL-2160; SEQ ID NO:1) from HCV-NS5a in the presence of IL-2. The spleen cells were then assayed for cytotoxic activity in a standard $^{51}$Cr release assay against peptide-sensitized target cells (L929) expressing class I, but not class II MHC molecules, as described in Weiss (1980) J. Biol. Chem. 255:9912–9917. Ratios of effector (T cells) to target (B cells) of 60:1, 20:1, and 7:1 were tested. Percent specific lysis was calculated for each effector to target ratio.

The results of the assays are shown in Tables 1 and 2. Table 1 demonstrates that immunization with plasmid DNA encoding an NS3NS4NS5a fusion protein activates CD8$^+$ T cells which recognize and lyse target cells displaying an NS5a epitope. Surprisingly the NS5a polypeptide of the NS3NS4NS5a fusion protein was able to activate T cells even though the NS5a polypeptide was present in a fusion protein.

Similarly, Table 2 demonstrates that delivery of the NS3NS4NS5a fusion protein to mice by means of an adenovirus vector also activates CD8$^+$ T cells which recognize and lyse target cells displaying an HCV NS5a epitope. Thus, immunization with either "naked" (plasmid) DNA encoding an NS3NS4NS5a fusion protein or adenovirus vector-encoded fusion protein can be used to activate HCV-specific T cells.

EXAMPLE 3

Immunization with DNA encoding an NS3NS4NS5a fusion protein activates HCV-specific CD8$^+$ T cells which express IFN-γ.

Intracellular Staining for Interferon-gamma (IFN-γ). Intracellular staining for IFN-γ was used to identify the CD8$^+$ T cells that secrete IFN-γ after in vitro stimulation with the NS5a epitope p214K9. Spleen cells of individual immunized mice were restimulated in vitro either with p214K9 or with a non-specific peptide for 6–12 hours in the presence of IL-2 and monensin. The cells were then stained for surface CD8$^+$ and for intracellular IFN-γ and analyzed by flow cytometry. The percent of CD8$^+$ T cells which were also positive for IFN-γ was then calculated. The results of these assays are shown in Tables 1 and 2. Table 1 demonstrates that CD8$^+$ T cells activated in response to immunization with plasmid DNA encoding an NS3NS4NS5a fusion protein also express IFN-γ. Immunization with an NS3NS4NS5a fusion protein encoded in an adenovirus also results in CD8$^+$ HCV-specific T cells which express IFN-γ, although to a lesser extent than immunization with a plasmid-encoded NS3NS4NS5a fusion protein (Table 2).

TABLE 1

HCV-NS5a-Specific CD8+ T Cells in Mice Immunized with NS5a or NS345a DNA

| | $^{51}$Cr Release Assay Percent Specific Lysis of Targets* | | | | Intracellular Staining for IFN-γ Percent of CD8+ T Cells Positive for IFN-g** | | | |
|---|---|---|---|---|---|---|---|---|
| | NS5a DNA | | NS345a DNA | | NS5a DNA | | NS345a DNA | |
| E:T ratio | p214K9 | — | p214K9 | — | p214K9 | — | p214K9 | — |
| 60:1 | 77 | 5 | 66 | 6 | | | | |
| 20:1 | 61 | 4 | 49 | 2 | 1.74 | 0.26 | 1.18 | 0.40 |
| 7:1 | 29 | 1 | 29 | 4 | | | | |

*Target cells (L929) were pulsed with p214K9 or media alone and labeled with $^{51}$Cr.
**Spleen cells were cultured with p214K9 or media alone for 12 hours in the presence of monensin.
p214K9 is a CTL epitopic peptide (2152-HEYPVGSQL-2160, SEQ ID NO:1) from HCV-NS5a '—' refers to the absence of peptide

TABLE 2

HCV-NS5a-Specific CD8+ T Cells Primed by Adenovirus or DNA Encoding for NS345a

| | $^{51}$Cr Release Assay Percent Specific Lysis of Targets* | | | | Intracellular Staining for IFN-γ Percent of CD8+ T Cells Positive for IFN-g** | | | |
|---|---|---|---|---|---|---|---|---|
| | NS5a DNA | | NS345a DNA | | NS5a DNA | | NS345a DNA | |
| E:T ratio | p214K9 | — | p214K9 | — | p214K9 | p214J | p214K9 | p214J |
| 60:1 | 76 | 2 | 55 | 5 | | | | |
| 20:1 | 85 | 2 | 22 | 3 | 3.24 | 0.13 | 0.25 | 0.09 |
| 7:1 | 62 | <1 | 10 | 3 | | | | |

*Target cells (L929) were pulsed with p214K9 or p214J and labeled with $^{51}$Cr.
**Spleen cells were cultured with p214K9 or p214J for 12 hours in the presence of monensin.
p214K9 is a CTL epitopic peptide (2152-HEYPVGSQL-2160, SEQ ID NO:1) from HCV-NS5a p214J is a control peptide (10 mer) from HCV-NS5a

EXAMPLE 4

Immunization with DNA encoding an NS3NS4NS5a fusion protein stimulates proliferation of HCV-specific CD4+ T cells.

Lymphoproliferation assay. Spleen cells from pooled immunized mice were depleted of CD8+ T cells using magnetic beads and were cultured in triplicate with either p222D, an NS5a-epitopic peptide from HCV-NS5a (2224-AELIEANLLWRQEMG-2238; SEQ ID NO:2), or in medium alone. After 72 hours, cells were pulsed with 1 μCi per well of $^3$H-thymidine and harvested 6–8 hours later. Incorporation of radioactivity was measured after harvesting. The mean cpm was calculated.

As shown in Table 3, immunization with a plasmid-encoded NS3NS4NS5a fusion protein stimulates proliferation of CD4+ HCV-specific T cells. Immunization with an adenovirus vector encoding the fusion protein also resulted in stimulated proliferation of CD4+ HCV-specific T cells (Table 4).

TABLE 3

HCV-NS5a-Specific CD4+ T Cells in Mice Immunized with NS5a or NS345a DNA
Mean CPM

| NS5a DNA | | NS345a DNA | |
|---|---|---|---|
| p222D | media | p222D | media |
| 4523 | 740 | 4562 | 861 |
| (x6.1) | | (x5.3) | | p222D is a CD4+ epitopic peptide (aa: 2224-AELIEANLLWRQEMG-2238, SEQ ID NO: 2) from HCV-NS5a

TABLE 4

HCV-NS5-Specific CD4+ T Cells Primed by Adenovirus or DNA Encoding for NS345a
Mean CPM

| NS345a Adeno | | NS345a DNA | |
|---|---|---|---|
| p222D | media | p222D | media |
| 896 | 357 | 1510 | 385 |
| (x2.5) | | (x3.9) | | p222D is a CD4+ epitopic peptide (aa: 2224-AELIEANLLWRQEMG-2238, SEQ ID NO: 2) from HCV-NS5a

EXAMPLE 5

Efficiency of NS345a-encoding DNA Vaccine Formulations to prime CTLs in mice.

Mice were immunized with either 10–100 μg of plasmid DNA encoding NS345a fusion protein as described in Example 1, with PLG-linked DNA encoding NS345a, described below, or with DNA encoding NS345a, delivered via electroporation (see, e.g., International Publication No. WO/0045823 for this delivery technique). The immunizations were followed by a booster injection 6 weeks later of $1 \times 10^7$ pfu vaccinia virus encoding NS5a, plasmid DNA encoding NS345a or plasmid DNA encoding NS5a each as described in Example 1.

for 6 hours. The microparticles were then separated by centrifugation, the pellet washed with TE buffer and the microparticles were freeze dried.

CTL activity and IFN-γ expression were measured by $^{51}$Cr release assay or intracellular staining as described in examples 2 and 3 respectively. The results are shown in Table 5.

Results demonstrate that immunization using plasmid DNA encoding for NS345a to prime mice results in activation of CD8+ HCV specific T cells.

TABLE 5

Efficiency of NS345a-Encoding DNA Vaccine Formulations to Prime CTLs in Mice

| NS345a DNA Vaccines | Boost | ICS for IFN-gamma (% CD8+ cells that are IFN-g+) | | # of mice tested | % responding | # of expts | fold increase vs. 'naked' DNA | CTL activity? |
|---|---|---|---|---|---|---|---|---|
| | | Mean | SdtdevP | | | | | |
| NS345a DNA | VVNS5a | 1.02 | 1.70 | 41 | 68% | 10 | N/A | YES |
| NS345a DNA | NS345a DNA | 0.02 | 0.04 | 22 | 5% | 5 | N/A | YES |
| NS345a DNA | NS5a DNA | 0.22 | 0.21 | 24 | 63% | 5 | N/A | YES |
| NS345a DNA eV (electroporation) | VVNS5a | 5.00 | 4.36 | 7 | 100% | 2 | 4.90 | YES |
| PLGNS345a DNA | VVNS5a | 2.65 | 2.54 | 6 | 100% | 2 | 2.60 | YES |
| PLGNS345a DNA | NS5aDNA | 0.33 | 0.24 | 15 | 80% | 3 | 1.50 | YES |

PLG-delivered DNA. The polylactide-co-glycolide (PLG) polymers were obtained from Boehringer Ingelheim, U.S.A. The PLG polymer used in this study was RG505, which has a copolymer ratio of 50/50 and a molecular weight of 65 kDa (manufacturers data). Cationic microparticles with adsorbed DNA were prepared using a modified solvent evaporation process, essentially as described in Singh et al., *Proc. Natl. Acad. Sci. USA* (2000) 97:811–816. Briefly, the microparticles were prepared by emulsifying 10 ml of a 5% w/v polymer solution in methylene chloride with 1 ml of PBS at high speed using an IKA homogenizer. The primary emulsion was then added to 50ml of distilled water containing cetyl trimethyl ammonium bromide (CTAB) (0.5% w/v). This resulted in the formation of a w/o/w emulsion which was stirred at 6000 rpm for 12 hours at room temperature, allowing the methylene chloride to evaporate. The resulting microparticles were washed twice in distilled water by centrifugation at 10,000 g and freeze dried. Following preparation, washing and collection, DNA was adsorbed onto the microparticles by incubating 100 mg of cationic microparticles in a 1 mg/ml solution of DNA at 4 C.

EXAMPLE 6

Immunization Routes and Replicon Particles SINCR (DC+) Encoding for NS345a

Alphavirus replicon particles, for example, SINCR (DC+) were prepared as described in Polo et al., *Proc. Natl. Acad. Sci. USA* (1999) 96:4598–4603. Mice were injected with $5\times10^6$ IU SINCR (DC+) replicon particles encoding for NS345a intramuscularly (IM) as described in Example 1, or subcutaneously (S/C) at the base of the tail (BoT) and foot pad (FP), or with a combination of ⅔ of the DNA delivered via IM administration and 1/3 via a BoT route. The immunizations were followed by a booster injection of vaccinia virus encoding NS5a as described in Example 1.

IFN-γ expression was measured by intracellular staining as described in Example 3. The results are shown in Table 6. The results demonstrate that immunization via SINCR (DC+) replicon particles encoding for NS345a by a variety of routes results in $CD8^+$ HCV specific T cells which express IFN-γ.

TABLE 6

Immunization Routes and SINCR (DC+) Replicon Particles Encoding NS345a
(all mice VVNS5a challenged)

| | | ICS for IFN-gamma (% CD8+ cells that are IFN-g+) | | | | |
|---|---|---|---|---|---|---|
| Vaccines | Immunization Route | Mean | SdtdevP | # of mice tested | # of expts | % responding mice |
| SINCR (DC+) 5 × $10^6$ | 100% IM (ta) | 1.11 | 0.63 | 3 | 1 | 100% |
| SINCR (DC+) 5 × $10^6$ | 100% S/C (BoT + FP) | 0.62 | 0.29 | 3 | 1 | 100% |
| SINCR (DC+) 5 × $10^6$ | ⅔ IM (ta) + ⅓ S/C (BoT) | 2.43 | 2.00 | 3 | 1 | 100% |

EXAMPLE 7

SINCR (DC+) Vs SINDC (LP) Replicon Particles Encoding for NS345a

Alphavirus replicon particles, for example, SINCR (DC+) and SINCR (LP) were prepared as described in Polo et al., *Proc. Natl. Acad. Sci. USA* (1999) 96:4598–4603. Mice were immunized with $1 \times 10^3$ to $1 \times 10^7$ IU of SINCR (DC+) or SINCR (LP) replicon particles encoding for NS345a, by intramuscular injection into the tibialis anterior, followed by a booster injection of $10^7$ pfu vaccinia virus encoding NS5a at 6 weeks.

IFN-γ expression was measured by intracellular staining as described in Example 3. Administration of an increase in the number of SINCR (DC+) replicon particles encoding NS345a resulted in an increase in % of CD8+ T cells expressing IFN-γ.

EXAMPLE 8

Alphavirus Replicon Priming, Followed by Various Boosting Regimes

Alphavirus replicon particles, for example, SINCR (DC+) were prepared as described in Polo et al., *Proc. Natl. Acad. Sci. USA* (1999) 96:4598–4603. Mice were primed with SINCR (DC+), $1.5 \times 10^6$ IU replicon particles encoding NS345a, by intramuscular injection into the tibialis anterior, followed by a booster of either 10–100 μg of plasmid DNA encoding for NS5a, $10^{10}$ adenovirus particles encoding NS345a, $1.5 \times 10^6$ IU SINCR (DC+) replicon particles encoding NS345a, or 107 pfu vaccinia virus encoding NS5a at 6 weeks.

IFN-γ expression was measured by intracellular staining as described in Example 3. The results are shown in Table 7. The results demonstrate that boosting with vaccinia virus encoding NS5a DNA results in the strongest generation of CD8+ HCV specific T cells which express IFN-γ. Boosting with plasmid encoding NS5a DNA also results in a good response, while lesser responses are noted with adenovirus NS345a or SINCR DC+boosted animals.

TABLE 7

Alphavirus Replicon Particle Priming, Followed by Various Boosting Regimens

| | | ICS for IFN-gamma (% CD8+ cells that are IFN-g+) | | | | |
|---|---|---|---|---|---|---|
| Vaccines | Boost | Mean | SdtdevP | # of mice tested | # of expts | % responding mice |
| SINCR (DC+) 1.5 × $10^6$ | NS5a DNA | 0.46 | 0.36 | 4 | 1 | 75% |
| SINCR (DC+) 1.5 × $10^6$ | Adeno NS345a (10 × $10^{10}$) | 0.04 | 0.04 | 4 | 1 | 25% |
| SINCR (DC+) 1.5 × $10^6$ | SINCR (DC+) 1.5 × $10^6$ | 0.06 | 0.06 | 8 | 2 | 25% |
| SINCR (DC+) 1.5 × $10^6$ | VVNS5a (1 × $10^7$) | 2.43 | 2.45 | 4 | 1 | 100% |

EXAMPLE 9

Alphaviruses Expressing NS345a

Alphavirus replicon particles, for example, SINCR (DC+) and SINCR (LP) were prepared as described in Polo et al., *Proc. Natl. Acad. Sci. USA* (1999) 96:4598–4603. Mice were immunized with $1 \times 10^2$ to $1 \times 10^6$ IU SINCR (DC+) replicons encoding NS345a via a combination of delivery routes (⅔ IM and ⅓ S/C) as well as by S/C alone, or with $1 \times 10^2$ to $1 \times 10^6$ IU SINCR (LP) replicon particles encoding NS345a via a combination of delivery routes (⅔ IM and ⅓ S/C) as well as by S/C alone. The immunizations were followed by a booster injection of $10^7$ pfu vaccinia virus encoding NS5a at 6 weeks.

IFN-γ expression was measured by intracellular staining as described in Example 3. The results are shown in FIG. 1. The results indicate activation of CD8+ HCV specific T cells.

EXAMPLE 10

Efficiency of NS5a Encoding DNA Vaccine Formulations to Prime CTLs in Mice

Mice were immunized with either 10–100 μg of plasmid DNA encoding NS5a as described in Example 1 or with PLG-linked DNA encoding NS5a as described in Example 5. The immunizations were followed by a booster injection at 6 weeks of either 10–100 μg of plasmid DNA encoding for NS5a, $10^{10}$ adenovirus particles encoding NS345a, 1.5×$10^6$ IU SINCR (DC+) replicon particles encoding NS345a, or $10^7$ pfu vaccinia virus encoding NS5a.

CTL activity and IFN-γ expression were measured by the methods described in Examples 2 and 3.

The results are shown in Table 8. The results demonstrate that priming with plasmid DNA encoding for NS5a or PLG-linked DNA encoding NS5a results in activation of CD8+ HCV specific T cells.

EXAMPLE 12

Administration of DNA via Separate Plasmids

Mice were immunized with 100 ug plasmid DNA encoding for NS345a or with 100 μg PLG-linked DNA encoding NS345a. Additionally, separate DNA plasmids encoding NS5a, NS34a, and NS4ab (33.3 μg each) were administered concurrently to another group of mice. Finally, PLG-linked DNA encoding NS5a, NS34a, and NS4ab (33.3 μg each) were administered concurrently to another group of mice.

TABLE 8

Efficiency of NS5a-Encoding DNA Vaccine Formulations to Prime CTLs in Mice

| NS5a Vaccines | Boost | ICS for IFN-gamma (% CD8+ cells that are IFN-g+) | | | | fold increase | | |
|---|---|---|---|---|---|---|---|---|
| | | Mean | SdtdevP | # of mice tested | % responding | # of expts | vs. 'naked' DNA | CTL activity? |
| NS5a DNA | VVNS5a | 1.67 | 1.49 | 8 | 100% | 3 | N/A | YES |
| NS5a DNA | NS5a DNA | 0.17 | 0.09 | 12 | 83% | 3 | N/A | YES |
| PLGNS5a DNA | NS5a DNA | 0.22 | 0.09 | 9 | 100% | 2 | 1.29 | YES |
| NS5a DNA | AdenoNS345a | 0.10 | 0.08 | 4 | 50% | 1 | N/A | NO |
| NS5a DNA | SINCRNS345a | 0.20 | 0.17 | 4 | 75% | 1 | N/A | YES |

EXAMPLE 11

Efficiency of NS345b-encoding DNA Vaccine Formulations to Prime CTLs in Mice

Mice were immunized with 10–100 μg of plasmid DNA encoding NS34b by intramuscular injection to the tibialis anterior or with PLG linked DNA encoding NS5a as described in Example 5. The immunizations were followed by a booster injection of plasmid DNA encoding for NS5a as described in Example 1.

CTL activity and IFN-γ expression were measured by the methods described in Examples 2 and 3.

The results are shown in Table 9. The results demonstrate that priming with plasmid DNA encoding NS345b or PLG-linked NS345b results in activation of CD8+ HCV specific T cells.

The immunizations were followed by a booster injection of 1×$10^7$ pfu vaccinia virus encoding NS5a, 6 weeks post first immunization.

Figure 2:
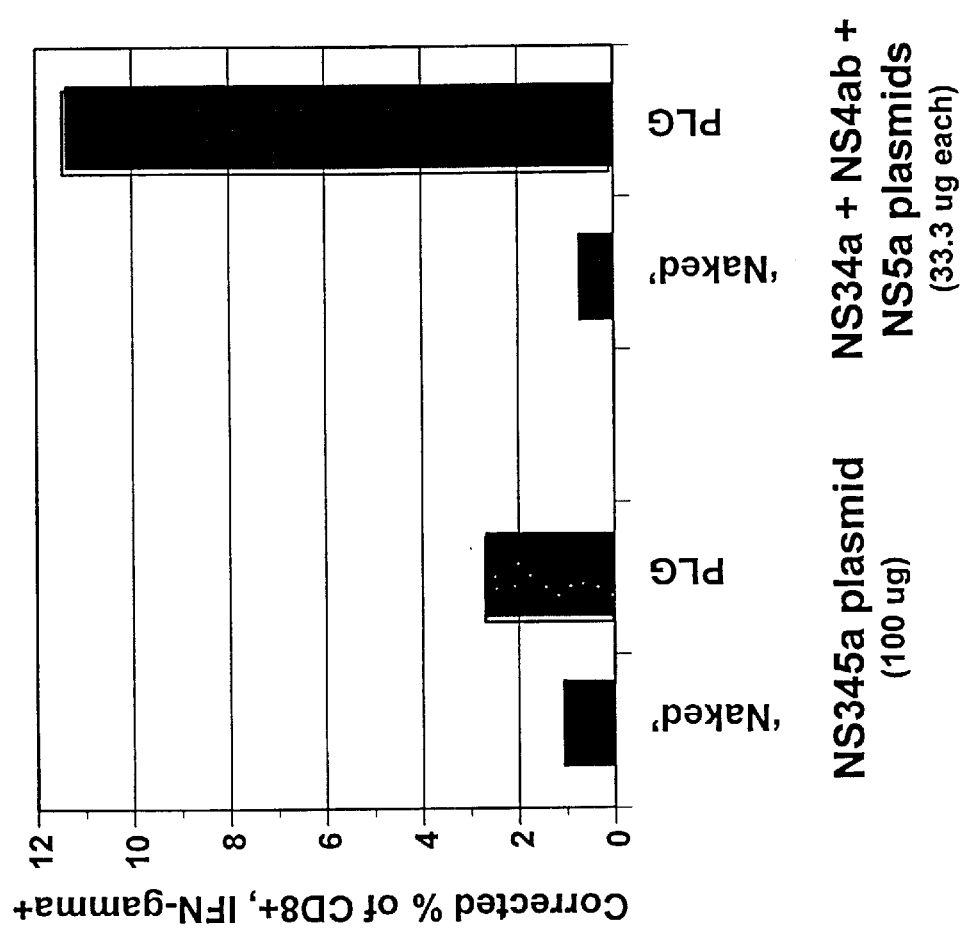
FIG. 2 shows IFN-γ expression generated in animals in response to delivery of plasmid DNA encoding NS3NS4NS5a ("naked"), PLG-linked DNA encoding NS3NS4NS5a ("PLG"), separate DNA plasmids encoding NS5a, NS34a, and NS4ab ("naked"), and PLG-linked DNA encoding NS5a, NS34a, and NS4ab ("PLG").

IFN-γ expression was measured by the method described in Example 3. The results are shown in FIG. 2. The results demonstrate a particularly vigorous response in the activation of CD8+ HCV specific T cells when the DNA is broken down into smaller sub units and linked to PLG.

Thus, HCV polypeptides; either alone or as fusions, to stimulate cell-mediated immune responses, are disclosed. Although preferred embodiments of the subject invention have been described in some detail, it is understood that obvious variations can be made without departing from the spirit and the scope of the invention as defined by the appended claims.

TABLE 9

Efficiency of NS345a-Encoding DNA Vaccine Formulations to Prime CTLs in Mice

| NS345 DNA Vaccines | Boost | ICS for IFN-gamma (% CD8+ cells that are IFN-g+) | | | | fold increase | | |
|---|---|---|---|---|---|---|---|---|
| | | Mean | SdtdevP | # of mice tested | % responding | # of expts | vs. 'naked' DNA | CTL activity? |
| NS345a DNA | NS5a DNA | 0.18 | 0.16 | 15 | 60% | 3 | N/A | YES |
| PLGNS345 DNA | NS5a DNA | 0.30 | 0.33 | 14 | 57% | 3 | 1.67 | YES |

What is claimed is:

1. A fusion protein comprising hepatitis C virus (HCV) proteins, wherein said HCV proteins consist of an NS3, an NS4, and an NS5a polypeptide of an HCV with one or more epitopes selected from the group consisting of an epitope shown in SEQ ID NO:1 and an epitope shown in SEQ ID NO:2.

2. A fusion protein comprising hepatitis C virus (HCV) proteins, wherein said HCV proteins consist of an NS3, an NS4, an NS5a, and NS5b polypeptide of an HCV with one or more epitopes selected from the group consisting of an epitope shown in SEQ ID NO:1 and an epitope shown in SEQ ID NO:2.

3. A fusion protein according to either of claims 1 or 2, wherein one of the HCV polypeptides is from a different strain of HCV than the other HCV polypeptides.

4. The fusion protein of claim 3 wherein each of the HCV polypeptides is from a different strain of HCV.

5. A composition comprising:

(a) a fusion protein according to either of claims 1 or 2; and (b) a pharmaceutically acceptable excipient.

6. A composition comprising:

(a) a fusion protein according to claim 4; and (b) a pharmaceutically acceptable excipient.

7. A method of activating T cells which recognize an epitope of an HCV polypeptide, comprising the step of:

contacting T cells with a fusion protein of either of claims 1 or 2, whereby a population of T cells are activated that recognizes an epitope selected from the group consisting of SEQ ID NO:1 and SEQ ID NO:2.

8. The method of claim 7 wherein the T cells are obtained from a mammal selected from the group consisting of a mouse, a baboon, a chimpanzee, and a human.

9. The method of claim 8 wherein the mammal is infected with an HCV.

10. The method of claim 8 wherein the mammal is not infected with an HCV.

11. The method of claim 7 wherein the population of T cells comprises $CD4^+$ T cells.

12. The method of claim 7 wherein the population of T cells comprises $CD8^+$ T cells.

13. The method of claim 12 wherein the $CD8^+$ T cells express interferon-γ.

14. The method of claim 12 wherein the $CD8^+$ T cells specifically recognize an epitope of an NS5a polypeptide.

15. The method of claim 14 wherein the epitope is selected from the group consisting of the epitopes shown in SEQ ID NO:1 and SEQ ID NO:2.

16. The method of claim 7 wherein the T cells comprise $CD8^+$ and $CD4^+$ T cells.

17. The method of claim 7 wherein the step of contacting further comprises contacting the T cells with an adjuvant.

18. The fusion protein of claim 1, wherein the one or more epitopes is an epitope shown in SEQ ID NO:1.

19. The fusion protein of claim 1, wherein the one or more epitopes is the epitope shown in SEQ ID NO:2.

20. The fusion protein of claim 1, wherein the one or more epitopes are epitopes shown in SEQ ID NO:1 and SEQ ID NO:2.

21. The fusion protein of claim 2, wherein the one or more epitopes is an epitope shown in SEQ ID NO:1.

22. The fusion protein of claim 2, wherein the one or more epitopes is the epitope shown in SEQ ID NO:2.

23. The fusion protein of claim 2, wherein the one or more epitopes are epitopes shown in SEQ ID NO:1 and SEQ ID NO:2.

24. The method of claim 23 wherein the population of T cells recognizes an epitope shown in SEQ ID NO:1.

25. The method of claim 7 wherein the population of T cells recognizes an epitope shown in SEQ ID NO:2.

26. The method of claim 7 wherein the population of T cells recognizes an epitope shown in SEQ ID NO:1 and SEQ ID NO:2.

* * * * *